United States Patent [19]

Tachi et al.

[11] 4,290,962
[45] Sep. 22, 1981

[54] NOVEL HYDROCORTISONE DERIVATIVE

[75] Inventors: Yasuhide Tachi, Tokyo; Kazuhiko Michishita, Omiya; Jozi Nakagami, Hasuda; Jiro Sawada, Tokyo; Mitsunori Washitake, Omiya; Yoshiaki Kamano, Tokyo, all of Japan

[73] Assignee: Taisho Pharmaceutical Co., Ltd., Tokyo, Japan

[21] Appl. No.: 24,111

[22] Filed: Mar. 26, 1979

[30] Foreign Application Priority Data

Mar. 29, 1978 [JP] Japan .................................. 53-36251

[51] Int. Cl.$^3$ .............................................. C07J 5/00
[52] U.S. Cl. .................................................. 260/397.45
[58] Field of Search ..................................... 260/397.45

[56] References Cited

U.S. PATENT DOCUMENTS

| | | | |
|---|---|---|---|
| 3,152,154 | 10/1964 | Ercoli et al. | 260/397.45 |
| 3,312,590 | 4/1967 | Elko et al. | 260/397.45 |
| 3,312,591 | 4/1967 | Elks et al. | 260/397.45 |
| 3,422,193 | 1/1969 | Shapiro et al. | 260/397.45 |

Primary Examiner—Elbert L. Roberts
Attorney, Agent, or Firm—George A. Loud

[57] ABSTRACT

17α-butyryloxy-11β-hydroxy-21-propionyloxy-4-pregnen-3,20-dione, i.e., hydrocortisone 17-butyrate 21-propionate of the present invention is prepared by acylating hydrocortisone 17-butyrate with propionic acid anhydride or halide. The compound of the present invention has excellent anti-inflammatory effect, percutaneous absorption and less side effect.

1 Claim, No Drawings

NOVEL HYDROCORTISONE DERIVATIVE

BACKGROUND

Various kinds of corticosteroids have recently been used as antirheumatic, anti-inflammatory, anti-allergic and antishock agents. Further, with respect to the administration route, they have recently become widely utilized externally as well as internally. These compounds includes those having a structure in which the corticosteroid is substituted by methyl, hydroxy, halogen(bromine, chlorine or fluorine), esterified hydroxy or acetonised hydroxy, and derivatives thereof. Accordingly, they have structures significantly modified or changed from structures of naturally occurring corticosteroids, such as, for example, triamcinolone, fluorocinolone acetonide, betamethasone, dexamethasone and their derivatives. Although these compounds are clinically effective, they tend to show side effects such as systemic action, and some therapeutists have been concerned about the side effects by the halogen-substituted structure. Furthermore, since each of these prior compounds has a structure considerably modified or changed from natural occurring corticosteroid structures, their mechanisms of metabolism and excretion in a living body are complicated. Accordingly, even if they are externally administered, they are not always safe.

Given such a background for these prior steroids, we have conducted research with a view to developing a steroid having a structure similar to that of a naturally occurring corticosteroid, and showing an excellent anti-inflammatory action on topical administration. As a result, we have found that 17α-butyryloxy-11β-hydroxy-21-propionyloxy-4-pregnen-3,20-dione, i.e., hydrocortisone 17-butyrate 21-propionate, has a much higher optical anti-inflammatory activity than other hydrocortisone derivatives and the commercially available steroidal agents for external administration.

DESCRIPTION AND PREFERRED EMBODIMENTS

The present invention relates to 17α-butyryloxy-11β-hydroxy-21-propionyloxy-4-pregnen-3,20-dione(I).

An object of the present invention is to provide a novel steroid, of a structure similar to naturally occurring corticosteroid structures, having excellent anti-inflammatory and less side effect upon external administration.

The compound(I) of the present invention may be synthesized according to various methods, preferably, according to the following method.

Hydrocortisone is reacted with a compound(II) represented by the general formula

CH₃CH₂CH₂C(OR)₃ wherein R is lower alkyl containing 1 to 5 carbon atoms, to give the corresponding 17α,21-(1'-alkoxy-1'-propylmethylenedioxy)-11β-hydroxy-4-pregnen-3,20-dione(III).

The cleaving reaction of the compound(III) with an acid such as oxalic acid or a mineral acid such as hydrochloric acid gives hydrocortisone 17-butyrate(IV). The acylation of the compound(IV) at its 21-hydroxy gives the compound(I) of the present invention. The acylation is generally carried out by using an acylating agent such as propionic acid anhydride or halide (bromide or chloride) in a solvent such as chloroform, methylene chloride, tetrahydrofuran, toluene or benzene in the presence of a base such as pyridine or triethylamine according to a conventional method. When an acid anhydride is used, the acylation is generally completed in pyridine in 2 to 3 hours at room temperature. When an acid halide is used, the acylation is, preferably, carried out under cooling at 0° to 10° C. for about 3 to 5 hours. After completion of the acylation, the reaction solution is poured into ice water and extracted with a solvent such as chloroform to give the compound(I). Alternatively, the reaction solution may be directly concentrated under reduced pressure to give the compound(I). The purification of the compound(I) obtained by each method may be carried out by recrystallization or column chromatography.

The compound(I) of the present invention has high topical anti-inflammatory action, and may be used for treatment of mammalian skin diseases such as acute or chronic eczema, seborrhoeic eczema, atopic dermatitis, infantile eczema, contact dermatitis and psoriasis vulgaris. For these purposes the compound(I) is administered topically in conventional dosage forms such as ointments, creams, lotions, liquid coatings, plasteres and powders prepared according to conventional pharmaceutical practice. The compound(I) may be used in the range of 0.01 to 5.0% by weight, preferably, 0.05 to 2.0% by weight in said conventional form.

The compound(I) shows very excellent anti-inflammatory and percutaneous absorption effects superior to those of other diesters of hydrocortisone. It is believed that these prominent effects are due to the types of ester groups at the 17 and 21 positions of hydrocortisone. Namely, although the compound(I) has a structure which is not too far from a natural occurring steroid structure and does not contain such substituents as halogens, the compound(I) has superior anti-inflammatory activity over other derivatives containing such substituents.

Vasoconstrictor test

Petrolatum-based ointments containing 0.1% of the compounds listed in Table 1, respectively, were prepared. These ointments were randomly applied to forearms of healthy adult male volunteers, and then they were removed at 4 hours after application. The degrees of vasoconstriction on the applied sites were recorded at 4 hours after removal of the ointments by four degrees as ++, +, ± and −, which were scored as 3, 2, 1 and 0, respectively. The scores of thirty volunteers for each ointment were summed up. The total and average scores of each test compound are shown in Table 1, wherein the total score is the value of the summed score of each ointment, and the average score is obtained by dividing the total value by the number of the volunteers.

TABLE 1

| compound | total score | average score |
|---|---|---|
| compound (I) | 74 | 2.47 |
| hydrocortisone 17,21-diacetate | 47 | 1.57 |
| hydrocortisone 17-acetate 21-propionate | 50 | 1.67 |
| hydrocortisone 17-acetate 21-butyrate | 10 | 0.33 |
| hydrocortisone 17-propionate 21-acetate | 54 | 1.80 |
| hydrocortisone 17,21-dipropionate | 61 | 2.03 |
| hydrocortisone 17-propionate 21-butyrate | 58 | 1.93 |
| hydrocortisone 17-butyrate 21-acetate | 55 | 1.83 |
| hydrocortisone 17,21-dibutyrate | 47 | 1.57 |

TABLE 1-continued

| compound | total score | average score |
| --- | --- | --- |
| hydrocortisone 17-valerate 21-acetate | 58 | 1.93 |
| hydrocortisone 17-valerate 21-propionate | 49 | 1.63 |
| hydrocortisone 17-valerate 21-butyrate | 38 | 1.27 |
| hydrocortisone 17-butyrate | 51 | 1.70 |
| betamethasone 17-valerate | 60 | 2.00 |
| placebo ointment | 2 | 0.07 |

Percutaneous absorption test

Percutaneous absorption of the compound(I) was examined using rat normal skin, and compared with those of hydrocortisone and hydrocortisone 17-butyrate.

1.0 ml of an aqueous solution containing 5 μg of the test compound was charged into a short glass tube fixed at an area on the rat abdominal surface (4 cm²) where the hair was cut off. After the specified time, the recovered amount of the test compound in the residual aqueous solution was determined by high pressure liquid chromatography.

Percutaneous absorption(%) of the test compound is calculated by the following expression $$\frac{5 \mu g - \text{Recovered amount } (\mu g)}{5 \mu g} \times 100$$

and results are shown in Table 2, wherein the mean and its standard error are given for each set of experiments.

TABLE 2

| Steroid | Time (hours) | | | |
| --- | --- | --- | --- | --- |
| | 1.0 | 3.0 | 5.0 | 7.0 |
| hydrocortisone | 1.8 | 4.6 | 5.6 | 6.5 |
| | ±1.4 | ±2.2 | ±2.5 | ±3.1 |
| hydrocortisone 17-butyrate | 4.5 | 7.5 | 11.4 | 14.1 |
| | ±1.8 | ±2.3 | ±3.8 | ±4.2 |
| compound (I) | 10.8 | 14.7 | 28.0 | 43.4 |
| | ±4.2 | ±3.1 | ±4.7 | ±5.7 |

Subacute toxicity test

The subacute toxicity of the compound(I) when it was administered to Wistar strain rats by the subcutaneous route consecutively for 30 days was investigated in contrast with hydrocortisone 17-butyrate and betamethasone 17-valerate, under the same experimental conditions. The test compounds were suspended in 5% gum arabic in appropriate concentrations. Animals were given the doses of 0.08, 0.4, 2.0, 10 and 50 mg/kg of the compound(I), 0.08, 0.4 and 2.0 mg/kg of hydrocortisone 17-butyrate, and 0.08, 0.4 and 2.0 mg/kg of betamethasone once daily, respectively. The animals serving as a control were administered 5% gum arabic for the same period. There were fatal cases in the males and females given 50 mg/kg of the compound(I). In all aminals treated by any test compound, as the dose level increased, such changes as depression of body weight gains, decreases in WBC count, increases in total cholesterol amount, and decreases in the thymus, adrenal, spleen and mesenteric lymphonodi weight were evident, and the atrophy of the thymus, adrenal, spleen and mesenteric lymphonodi were remarkable when examined histopathologically. At the same dosage level, changes produced by betamethasone 17-valerate were severer than those by others. In the urinalysis, no changes were seen in the treated groups as compared with the control group. And, in the recovery test performed 30 days after the termination of the drug administration, changes of the organs have almost recovered.

It was concluded that the subacute toxicity of steroids by subcutaneous administration was in the following order: betamethason 17-valerate > hydrocortisone 17-butyrate ≧ compound(I).

The present invention is further illustrated by the following detailed example.

EXAMPLE (1) A solution of hydrocortisone (5 g) in dimethylformamide (5 ml) containing ethyl orthobutyrate (5 ml) and p-toluenesulfonic acid (200 mg) was heated with stirring at 110° C. for 3 hours. To the reaction mixture pyridine (3 ml) was added. After evaporation of the solvent the residue was purified by column chromatography over silica gel and recrystallization from acetone-n-hexane to yield hydrocortisone 17, 21-cyclic ethyl orthobutyrate (3 g). m.p. 166°-167° C.

(2) A solution of hydrocortisone 17, 21-cyclic ethyl orthobutyrate (2.5 g) in methanol (200 ml) containing saturated aqueous oxalic acid (2.5 ml) was allowed to stand at room temperature overnight. After the reaction was complete, the mixture was purified by column chromatography on silica gel with chloroform and recrystallization from acetone-n-hexane to give hydrocortisone 17-butyrate (1.2 g). m.p. 208°-210° C.

(3) To a solution of hydrocortisone 17-butyrate (1.0 g) in pyridine (5 ml) propionic acid anhydride (2 ml) was added at 0° C., and the mixture was allowed to stand at room temperature overnight. The reaction mixture was poured into ice-water (100 ml) and extracted with chloroform. The chloroform solution was washed with dil. HCl and water and dried over anhydrous sodium sulfate. Evaporation of the chloroform and recrystallization of the residue from benzene-n-hexane gave colorless crystals (1 g), m.p. 79°-84° C. Moreover, a solution of these crystals in ethanol was added dropwise to water with stirring, and the precipitate formed was filtrated and dried over phosphorus pentoxide in vacuo at room temperature to give hydrocortisone 17-butyrate 21-propionate as colorless crystalline powders, m.p. 117°-117.5° C. (decomp. at 265°-268° C.).

NMR: (in $C_5D_5N$); 1.00(3H, s), 1.00-1.30(6H, m), 1.43(3H, s), 4.48(1H, m), 4.74(2H, d.d., J=18 Hz, 6 Hz), 5.65(1H, s).

What we claim is:

1. 17α-butyryloxy-11β-hydroxy-21-propionyloxy-4-pregnen-3,20-dione.

* * * * *

UNITED STATES PATENT AND TRADEMARK OFFICE

CERTIFICATE EXTENDING PATENT TERM
UNDER 35 U.S.C. § 156

PATENT NO.      :   4,290,962

ISSUED          :   September 22, 1981

INVENTOR(S)     :   Yasuhide Tachi et al.

PATENT OWNER    :   Taisho Pharmaceutical Co., Ltd.

PRODUCT         :   PANDEL Cream (hydrocortisone cream)

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of Five years from March 26, 1999, the original expiration date of the patent with all rights pertaining thereto as provided by 35 U.S.C. § 156(b).

I have caused the seal of the Patent and Trademark Office to be affixed this 7th day of June 1999.

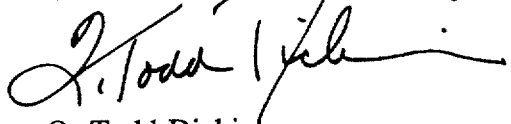

Q. Todd Dickinson
Acting Assistant Secretary of Commerce and
Acting Commissioner of Patents and
Trademarks